US006961911B2

(12) United States Patent
Suzuki et al.

(10) Patent No.: US 6,961,911 B2
(45) Date of Patent: Nov. 1, 2005

(54) DISPLAY METHOD AND APPARATUS FOR DISPLAYING THREE-DIMENSIONAL DATA AS A COMBINATION OF THREE SECTIONAL IMAGES, RECORDING MEDIUM IN WHICH A COMPUTER READABLE PROGRAM IS SAVED FOR EXECUTING THE METHOD, AND COMPUTER READABLE FOR EXECUTING THE METHOD

(75) Inventors: Masakazu Suzuki, Kyoto (JP); Hideki Yoshikawa, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 720 days.

(21) Appl. No.: 09/844,801

(22) Filed: Apr. 27, 2001

(65) Prior Publication Data

US 2002/0015006 A1 Feb. 7, 2002

(30) Foreign Application Priority Data

| Apr. 28, 2000 | (JP) | ................................. 2000-129629 |
| Dec. 8, 2000 | (JP) | ................................. 2000-374378 |

(51) Int. Cl.[7] .............................................. G06F 3/00
(52) U.S. Cl. ..................................... 715/858; 715/850
(58) Field of Search ........................ 715/858, 850–852, 715/859, 754, 757, 756, 771–773, 970, 964, 719–726, 804, 767; 345/804, 767, 765, 808, 809, 817, 853–854, 836, 782, 850–852, 856–862

(56) References Cited

U.S. PATENT DOCUMENTS

| 5,454,069 A | * | 9/1995 | Knapp et al. ................ 345/420 |
| 5,623,583 A | * | 4/1997 | Nishino ....................... 345/420 |
| 5,821,925 A | * | 10/1998 | Carey et al. .................. 715/757 |
| 5,954,414 A | * | 9/1999 | Tsao ............................... 353/7 |
| 5,956,028 A | * | 9/1999 | Matsui et al. ................ 715/757 |
| 6,064,904 A | * | 5/2000 | Yanof et al. ................. 600/414 |
| 6,095,976 A | * | 8/2000 | Nachtomy et al. ........... 600/443 |
| 6,115,027 A | * | 9/2000 | Hao et al. .................... 715/858 |
| 6,149,592 A | * | 11/2000 | Yanof et al. ................. 600/427 |
| 6,152,878 A | * | 11/2000 | Nachtomy et al. ........... 600/467 |
| 6,263,093 B1 | * | 7/2001 | Mochizuki ................... 382/128 |
| 6,313,855 B1 | * | 11/2001 | Shuping et al. .............. 345/854 |
| 6,339,440 B1 | * | 1/2002 | Becker et al. ............... 715/858 |
| 6,342,889 B1 | * | 1/2002 | Callahan ...................... 345/427 |
| 6,392,675 B1 | * | 5/2002 | Becker et al. ............... 715/858 |
| 6,525,847 B2 | * | 2/2003 | Popovich et al. ............. 359/15 |
| 6,573,855 B1 | * | 6/2003 | Hayakawa et al. ............ 342/22 |
| 6,614,453 B1 | * | 9/2003 | Suri et al. .................... 715/764 |
| 6,671,538 B1 | * | 12/2003 | Ehnholm et al. ............ 600/425 |
| 6,674,449 B1 | * | 1/2004 | Banks et al. ................. 715/740 |
| 6,677,944 B1 | * | 1/2004 | Yamamoto ................... 345/422 |

FOREIGN PATENT DOCUMENTS

EP 0 930 046 A2 * 7/1999 ............ A61B/6/00

* cited by examiner

Primary Examiner—Steven P. Sax
(74) Attorney, Agent, or Firm—Koda & Androlia (57) ABSTRACT

A method and apparatus for displaying three-dimensional CT (Computed Tomography) data as a combination of three sectional images defined by an X-section, a Y-section and a Z-section orthogonalizing each other and the recoding medium saving a program for realizing the method are disclosed together. According to the method, when a cursor on one of the three sectional images is moved, another sectional image sequentially changed corresponding to a movement of the cursor.

24 Claims, 12 Drawing Sheets

DISPLAY METHOD AND APPARATUS FOR DISPLAYING THREE-DIMENSIONAL DATA AS A COMBINATION OF THREE SECTIONAL IMAGES, RECORDING MEDIUM IN WHICH A COMPUTER READABLE PROGRAM IS SAVED FOR EXECUTING THE METHOD, AND COMPUTER READABLE FOR EXECUTING THE METHOD

BACKGROUND OF THE INVENTION

1. Field of the Invention

The present invention relates to a display method and a display device for changeably displaying sectional images in the form of a combination of three sectional images, together with cursors specifying their corresponding section of the images, following the movement of one or two cursor of three sectional images and a recording medium saving computer readable program for realizing the method.

2. Description of the Related Art

Although a method for displaying a sectional image relative to optionally indicated section by remaking three-dimensional data obtained by such as CT imaging has been known, conventional methods were carried out in a manner that a sectional image of required section was printed on a film of a predetermined size or a sectional image for which necessary computing were performed every time for indicated section was displayed on a screen of a display apparatus.

However, in the former method, the number of displaying images would be limited, thus it was inferior in mobility because, when another sectional images were required by seeing the images displayed on the screen, it was necessary to again print on a film the required sectional images by remaking from three dimensional CT image data.

The applicant think it easy for understanding that such sectional images, including the case of displaying on a screen of a display apparatus, are displayed in a manner that three images of three sections relative to desired parts orthogonalizing each other are displayed contrasting with each other, however, such displaying method and apparatus was not thought out as long as the applicant knows.

Further, in conventional method, it was necessary a certain time for displaying the sectional image of required section on a screen of the display apparatus, which prevents rapid displaying thus cause impatience for the users.

SUMMARY OF THE INVENTION

The present invention has been proposed to solve the above-mentioned problems.

Accordingly an object of the invention is to provide a display method of three sectional images in which three-dimensional images understandable by intuition can be displayed and selection for desirable sectional image, which are viewed from desired directions for examination, can be easily carried out by moving of one or two cursor specifying the corresponding section of the images.

The second object of the present invention to provide a display device for displaying three sectional images by caring out the present method.

Further object of the present invention is to provide a recording medium in which computer readable program for realizing the present method is saved.

In order to achieve the first object of the present invention, a display method of displaying, as a combination, three sectional images of an X-section, a Y-section, and a Z-section, orthogonalizing each other, by processing a three-dimensional data obtained by such as CT imaging is provided, wherein said method characterized by following steps of; preparing in advance sectional images of sections parallel to said X-section, Y-section, and Z-section, said sectional images being slice off data from said three-dimensional data at a predetermined interval, displaying on three display parts as a three sectional displaying mode a X-sectional image, a Y-sectional image, and a Z-sectional image, each selected from said prepared sectional images, together with an X-cursor, a Y-cursor, and a Z-cursor, each of which specifies a section of said corresponding sectional images, and when, on any one of said three display parts, at least one of said cursors displayed together with said sectional images is moved, sequentially changing a sectional image to be displayed corresponding to the moved cursor on another display part different from the display part where the cursor was moved, following the moving of the cursor, in a manner that said sectional image to be displayed on said other display part is selected from said sectional images.

And in order to achieve the second object of the present invention, there provided a display apparatus for displaying three-dimensional data as a combination of three sectional images of an X-section, a Y-section, and a Z-section, orthogonalizing each other, by processing the three-dimensional data obtained by such as CT imaging, comprising;

an image memory for saving prepared sectional images of sections parallel to said X-section, Y-section, and Z-section, said sectional images being slice off data from said three-dimensional data at a predetermined interval, and display controlling means with three display parts for displaying a combination of an X-sectional image, a Y-sectional image, and a Z-sectional image as a three sectional displaying mode, each sectional image being selected from said sectional images previous prepared, together with an X-cursor, a Y-cursor, and a Z-cursor, each of which specifies a section of said corresponding sectional images, whereby when, on any one of said three display parts, at least one of said cursors displayed together with said sectional images is moved, a sectional image to be displayed corresponding to the moved cursor on another display part different from the display part where the cursor was moved is sequentially changed, following the moving of the cursor, in a manner that said sectional image to be displayed on said other display part is selected from said sectional images.

Still further in order to achieve the other object of the present invention, a recording medium saving the computer readable program for carrying out the present method are also provided.

DETAILED DESCRIPTION OF THE INVENTION

Now the embodiments of the present invention will be described referring to the attached drawings.

Figure 1:
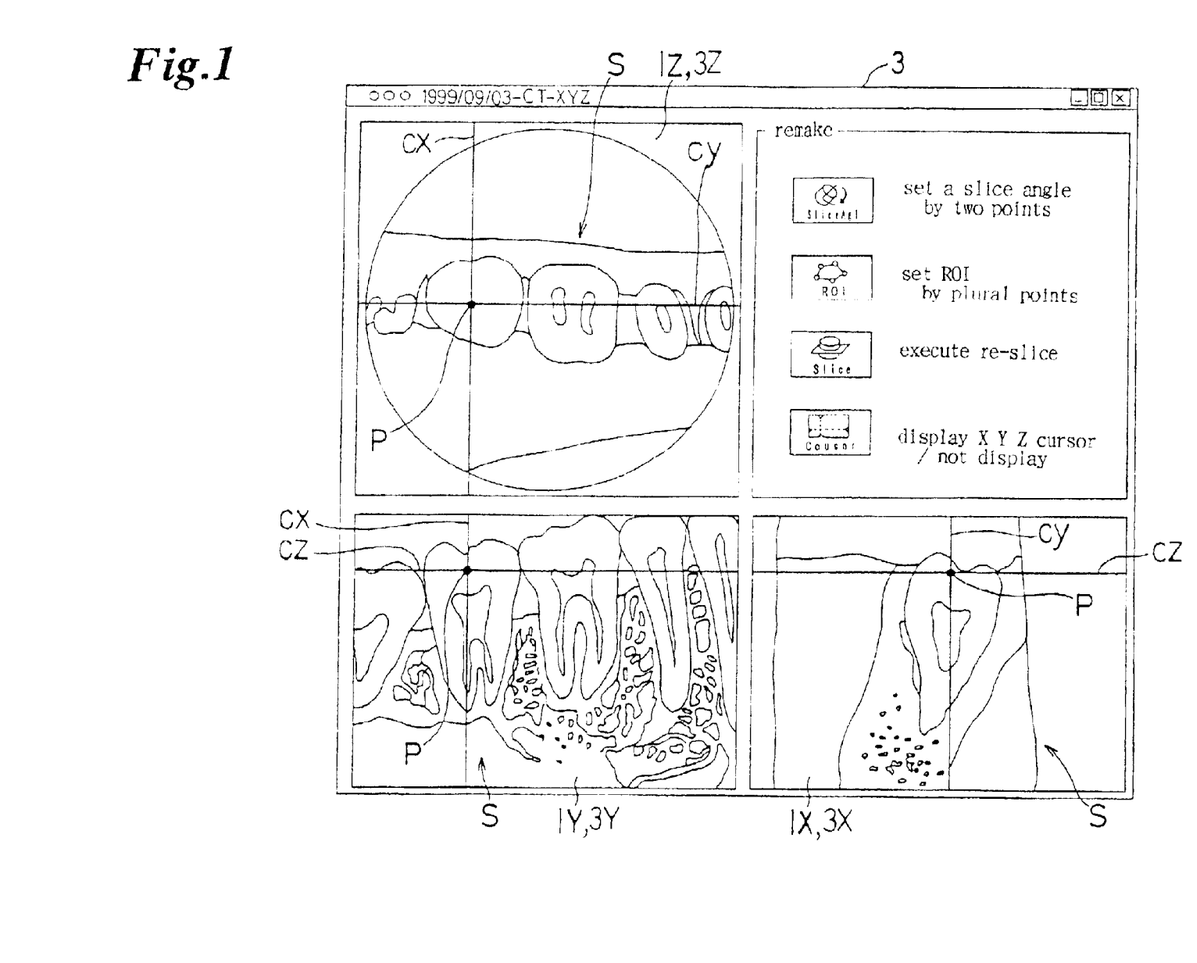
FIG. 1 shows one example of a screen shown by a display method of sectional images of the present invention.
Figure 2:
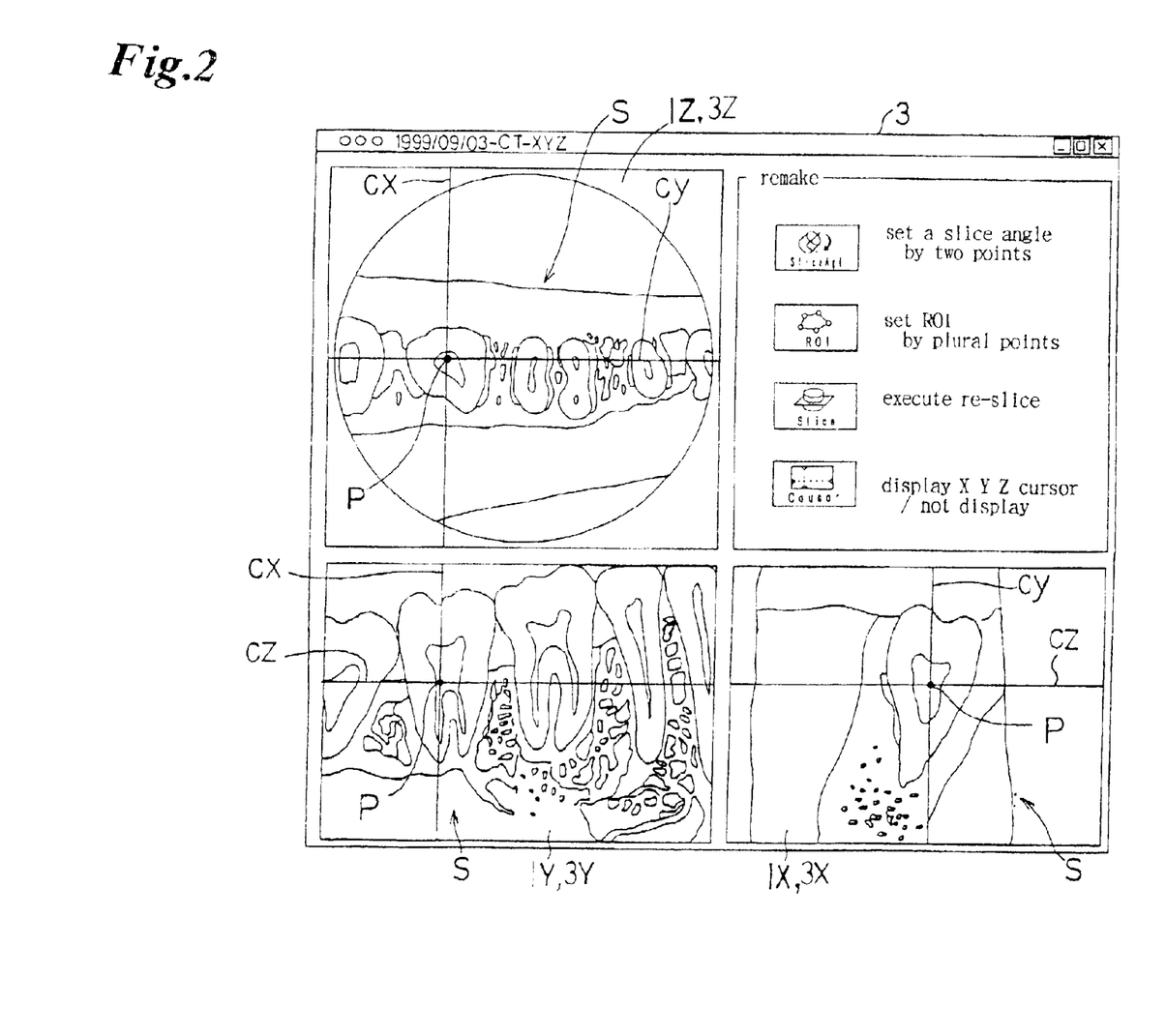
FIG. 2 shows another example of a screen shown by a display method of sectional images of the present invention.
Figure 3:
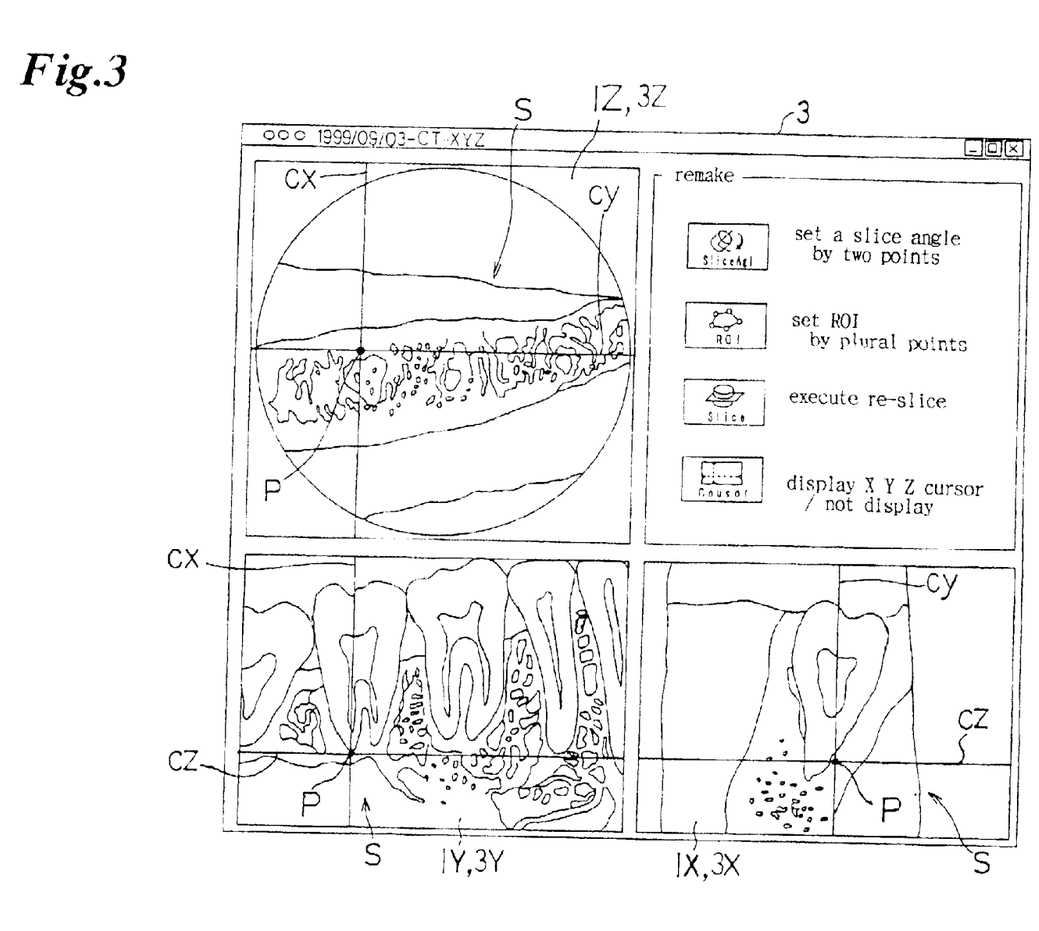
FIG. 3 shows still another example of a screen shown by a display method of sectional images of the present invention.

FIG. 1, FIG. 2 and FIG. 3 show examples of a screen shown by a display method of sectional images of the present invention.

In these figures, the reference mark S shows a three-dimensional area as an object for displaying sectional images of the present invention and in this case a part of dental arch which is an object of dental care, is used as an example.

The reference numeral 3 shows a screen on which images such as sectional images of the three-dimensional area S are displayed, and IX, IY, IZ show an X-sectional image, a Y-sectional image, and a Z-sectional image of the three-dimensional area S displayed on the screen 3 respectively.

The three parts, on which sectional images IX, IY, IZ are displayed also named display part 3X, 3Y and 3Z.

The reference marks cx, cy, and cz show an X-cursor, a Y-cursor, and a Z-cursor each of which is a projector line of other sections such as an X-section, a Y-section, and a Z-section for hewing or slice out X-sectional images, Y-sectional images, and Z-sectional images respectively. The reference mark P is an optional point in the three-dimensional area S, which equals nearly to crossing point of the X, Y, Z-sections.

In this example, first an optional point P is selected and later nearest sectional images IX, IY, IZ to the point P are selected from prepared sectional images and displayed as the figure. But, they can first select optional sectional images IX, IY, IZ and in this case, a point P equals accurate to crossing point of the X, Y, Z-sections.

In these figures, a Z-sectional image IZ, a Y-sectional image IY, and an X-sectional image IX all of which include this point P are displayed in array like normal plane view, front view, and side view as three sectional displaying mode. Sectional images of the point seen from top, front, and side are displayed comparatively so that they are easily understood by intuition.

The X-cursor cx, the Y-cursor cy, and the Z-cursor cz are shown for the Z-sectional image IZ, the Y-sectional image IY, and the X-sectional image IX respectively. Namely, the X-cursor cx and the Y-cursor cy are displayed on the Z-sectional image IZ, the Z-cursor cz and the X-cursor cx are displayed on the Y-sectional image IY, and the Y-cursor cy and the Z-cursor cz are displayed on the X-sectional image IX.

The X-cursor cx shows a position of an X-section and the Y-cursor cy shows a position of a Y-section on the Z-sectional image IZ, the Z-cursor cz shows a position of a Z-section and the X-cursor shows a position of a X-section on the Y-sectional image IY, and the Y-cursor cy shows a position of a Y-section and the Z-cursor cz shows a position of a Z-section on the X-dimensional image IX.

Therefore, relative relation of three sectional images of the X-sectional image, the Y-sectional image and the Z-sectional image is easily understood by intuition.

Comparing the screens in FIG. 1, FIG. 2, and FIG. 3, only the image of the Z-sectional image IZ at upper left is changed and the X-cursor cx and Y-cursor cy aren't changed on the Z-sectional image IZ. Namely, the X-sectional image IX and the Y-sectional image IY aren't changed in these figures.

On the other hand, only the Z-cursor cz on lower Y-sectional image IY and only the Z-cursor cz on lower X-sectional image IX are synchronously moved from up to down. It is well understood that the cursor cz shows a position of the Z-section intersecting the Y-section and the X-section each of which is a base of the Y-sectional image IY and the X-sectional image IX respectively.

In fact the Z-cursor cz is, for example, pressed to be kept and moved downward on the Y-sectional image IY in FIG. 1, then the Z-cursor cz on the X-sectional image IX is synchronously moved accordingly, and the Z-sectional images IZ hewn or sliced out on the Z-section designated by the cursor cz are sequentially displayed. FIG. 2 shows a screen on the way and FIG. 3 shows a screen when both cursors cx and cy are finally released.

Such sequential display while moving the cursors can be executed for the Y-sectional image IY and the X-sectional images IX.

Any one of the X-cursor showing a position of the X-section, the Y-cursor showing a position of the Y-section, and the Z-cursor showing a position of the Z-section can be moved in parallel on the screen displayed in three sectional displaying mode by means of a mouse and sectional images corresponding to the moved cursor are displayed sequentially in accordance with the movement of the mouse. Therefore, it is easy for an operator to find a suitable sectional image.

In spite of moving the cursor one by one as mentioned above, intersection points (corresponding to the reference mark P in the figures) of the X-cursor cx and the Y-cursor cy, the Z-cursor cz and the X-cursor cx, the Y-cursor cy and the Z-cursor cz, each of which are orthogonalized on the Z-sectional image IZ, the Y-sectional image IY, and the X-sectional image IX respectively are held and moved so that these two cursors can be simultaneously moved. Accordingly sectional images hewn out for two sections corresponding to the moved two cursors in advance can be sequentially displayed respectively.

In this case it is convenient that two sectional images can be displayed sequentially.

Further, for displaying the X-sectional image IZ, the Y-sectional image IY, and the X-sectional image IX on the screen 3, image display conditions can be adjusted by means of an image condition control means which is usually provided. When such adjustments, especially contrast and brightness of the image, are same among three images, contrast and entire brightness of images can be unified so that such images become easily viewable and suitable for medical examination.

As for image display, adjustment of gamma coefficient, namely coefficient showing relation of shading of each color of black and white or three primary colors on data and what a human actually sees the displayed screen, is important. An image most similar to a real thing can be sensed by human eyes by selecting appropriate gamma coefficient corresponding to the kinds of images. Further in such a case, gamma coefficient can be made the same and three images which are similar to a real thing in the same degree can be shown so that such images are suitable for medical examination. When a button of "set ROI on plural points" is clicked on the screen 3, the screen becomes a border designation mode. For example when plural points are designated at random by a mouse for a border of teeth including the point P on the X, Y, Z-sectional images in FIG. 1, the data designated by the plural points is extracted from the three-dimensional area and three dimensional oblique perspective figure can be obtained.

Figure 4:
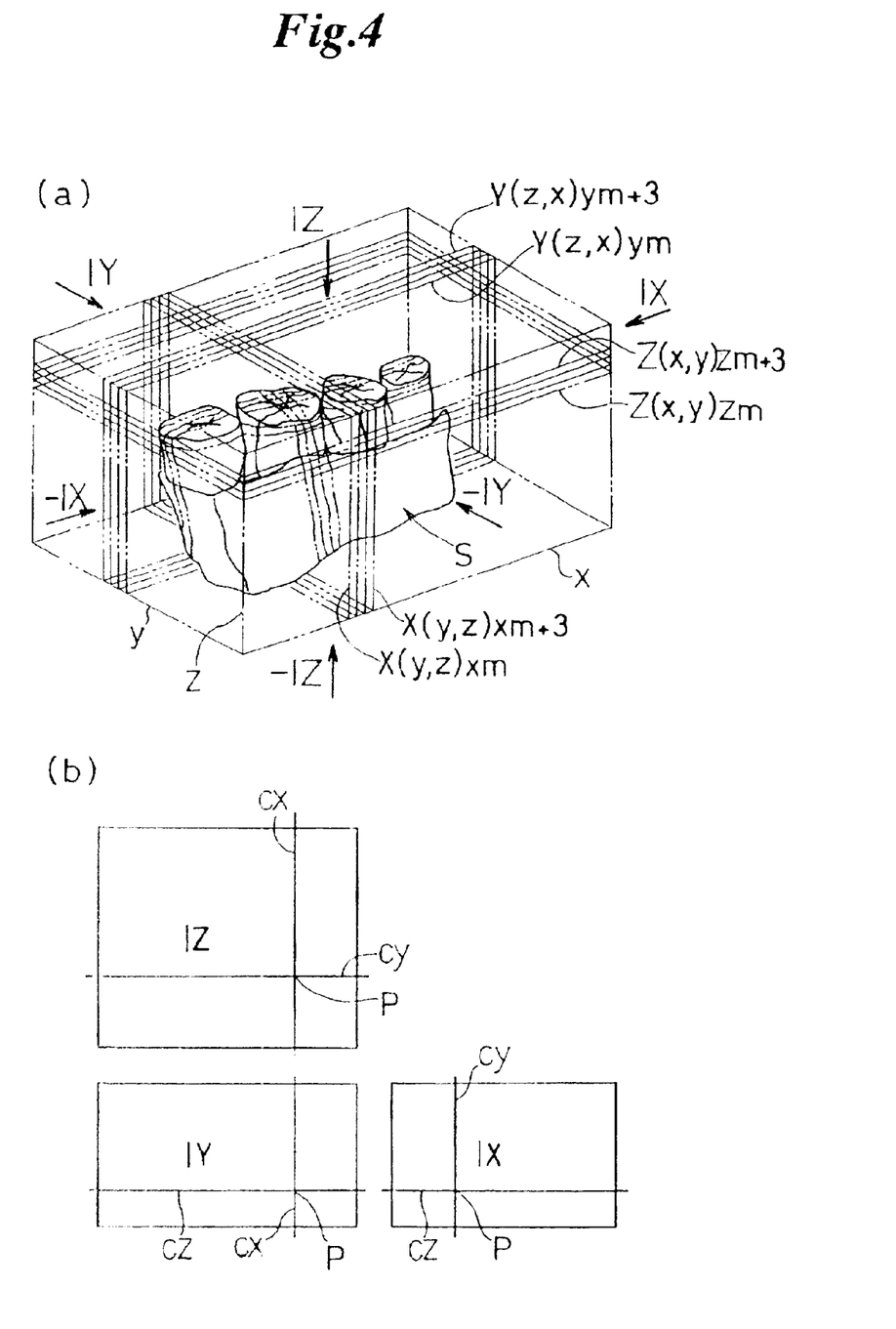
FIG. 4(a) is a conceptual diagram showing hewing out method of sectional images according to a display method of sectional images of the present invention.
FIG. 4(b) is a conceptual diagram showing one example of the display method of sectional images of the present invention.

FIG. 4(a) is a conceptual diagram showing hewing out of method of sectional images according to a display method of sectional images of the present invention, and FIG. 4(b) is a conceptual diagram showing one example of the display method of sectional images of the present invention. As the same reference numerals and marks are allotted to the member as explained before, their explanations are omitted hereinafter.

The three-dimensional area S in FIG. 4(a) is the same one explained in FIG. 1, FIG. 2, and FIG. 3. Three-dimensional CT data has been obtained for each point constructing the three-dimensional area S and when xyz coordinate system is set as shown in the figure, a voxel value V (x, y, z) of an optional point (x, y, z) is determined.

Hewing out of X-sectional images of an X-section which is perpendicular to an x-axis x is done by determining an x-coordinate (x=xm) and by aligning a voxel value V (xm, y, z) on the X-section having the x-coordinate on a two-dimensional flat surface. Thus obtained X-sectional image is described as X(y, z)xm.

According to the method, X(y, z)x0, X(y, z)x1, . . . , X(y, z)xm, X(y, z)xm+1, X(y, z)xm+2, X(y, z)xm+3, . . . , X(y, z)xn are obtained.

In the same manner, Y-sectional images, Y(z, x)y0, Y(z, x)y1, . . . , Y(z, x)ym, Y(z, x)ym+1, Y(z, x)ym+2, Y(z, x)ym+3, . . . , Y(z, x)yn, are obtained for the Y-section perpendicular to a y-axis y. Z-sectional images, Z(x, y)z0, Z(x, y)z1, . . . , Z(x, y)zm, Z(x, y) zm+1, Z(x, y) zm+2, Z(x, y)zm+3, . . . , Z(x, y) zn, are obtained for the Z-section perpendicular to a z-axis z.

Any one of thus obtained X-sectional images, Y-sectional images, and Z-sectional images including an optional point P in the three-dimensional area S is taken out and its view is shown in FIG. 4(b) together with the X-cursor cx, the Y-cursor cy, and the Z-cursor cz. Its specific examples are shown in FIG. 1, FIG. 2 and FIG. 3.

Such a three-section display of sectional images isn't limited to FIG. 4(b) and it may be displayed like an alignment in FIG. 5(a) and FIG. 5(b).

In FIG. 5(a) and FIG. 5(b), "–IZ" and "–IX" show screens in which sectional images are seen from negative direction of corresponding z-axis and x-axis as shown in FIG. 4(a).

Figure 5:
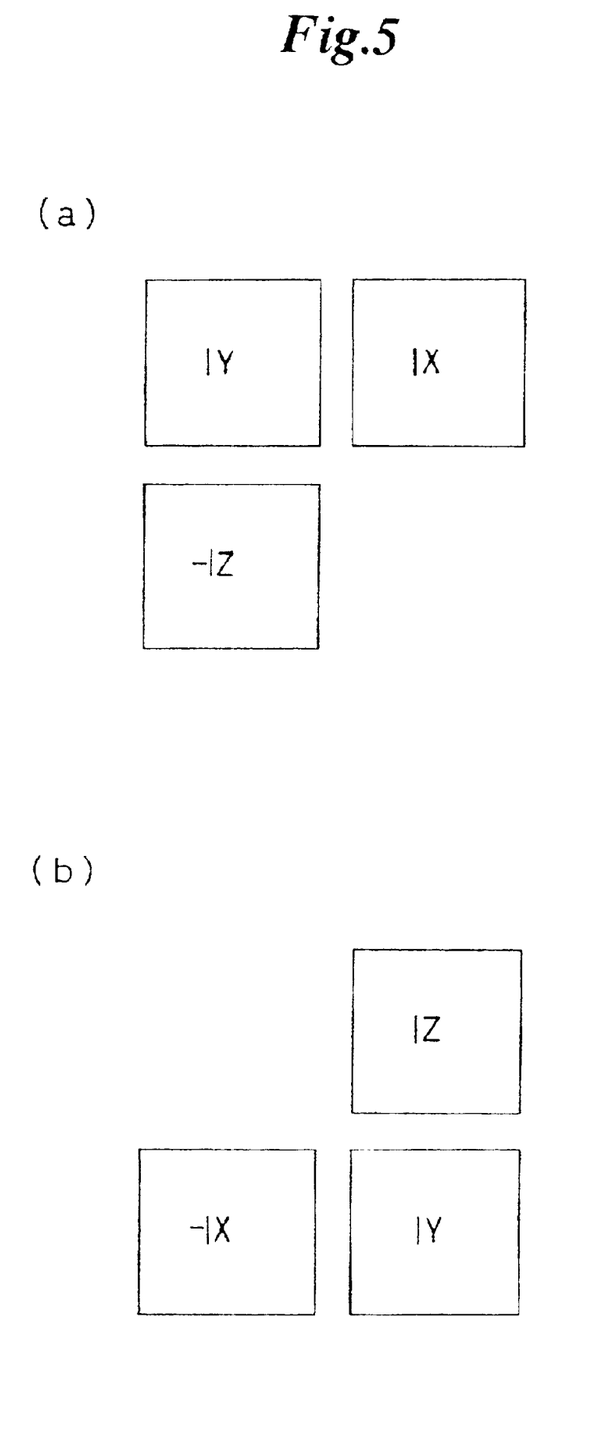
FIG. 5(a) and FIG. 5(b) show another example of a display method of sectional images according to a display method of sectional images of the present invention.

As seen from FIG. 4(a), there are two kinds of sectional images for one section, namely a sectional image seen from positive direction of a coordinate axis and a sectional image seen from negative direction of a coordinate axis. Those images can be combined for three directions of x, y and z-axes so that there is cubic of 2, namely 8, types of display alignment in principle as display alignments as shown in FIG. 5 and any type may be used depending on a medical examination purpose.

Two sectional images may be displayed in combination in spite of three sectional images.

Next a display system for achieving the above-mentioned display method of the sectional images of the present invention.

FIG. 6(a) is an external front view showing one example of display system of sectional images of the present invention, and FIG. 6(b) is a block diagram of its essential part.

A display system 10 is provided with a central processing unit 1 for controlling and processing the entire system, an input/output device 2 for controlling input and output of data to the central processing unit 1, a screen 3 for displaying the data from the input/output port 2, and a keyboard/mouse 4 comprising a keyboard 4A and a mouse 4B for receiving data and input of operational direction.

It is further provided with a supplementary input/output device 5 for receiving a unified program and input data such as three-dimensional CT data of a three-dimensional area obtained by CT imaging from outside and for outputting the data produced in the display system 10 outside, a memory 6 for storing programs and associated data required for controlling the display system 10, an image producing means 7 for hewing or slicing out sectional images of a desired section from the three-dimensional CT data given for the three-dimensional area, a rotating means for coordinate axis 8 for rotating a coordinate axis when a sectional image is hewn or sliced out as mentioned hereinafter, and a recording medium 9 for recording and storing the program and so on which achieves the above-mentioned display method, the recording medium 9 being able to be read out and written by the supplementary input/output device 5.

Sectional images and so on are shown on the screen 3 and displayed element on the screen 3 can be moved by means of the mouse 4B on the screen 3.

The memory 6 comprising a hard disk and so on can store and record data rewritably and is provided with a CT data memory 6a for storing three-dimensional CT data of the three-dimensional area and an image memory 6b for storing remade sectional images.

The functions of the image producing means 7 and the rotating means for coordinate axes 8 are practically achieved when associated devices are controlled by the central processing unit 1 based on the program stored in the memory 6.

The recording medium 9 includes a rewritable or non-rewitable recording medium such as CD-ROM, CD-R, CD-RW, MO, DVD, DVD-R, DVD-RAM and so on.

By the way, the screen 3 with display parts 3X, 3Y, 3Z and the image producing means 7 and other relating parts set up a display controlling means.

Thus constructed display system 10 for sectional images remakes the three-dimensional CT data of the three-dimensional area stored in the CT data memory 6a and stores the X-sectional images IX, the Y-sectional images IY, and Z-sectional images IZ hewn out at a fixed time interval in the image memory 6b according to the program for achieving the above-mentioned method for displaying sectional images stored in the memory 6. The sectional images are shown on the screen 3 as explained in FIG. 1, FIG. 2, and FIG. 3 and sectional images corresponding to the moved cursor can be sequentially displayed accompanying movement of the X-cursor cx, Y-cursor cy, and Z-cursor cz on the screen 3.

In this system display of three sectional images in array as three sectional displaying mode and display of sectional images in serial as a list displaying mode accompanying movement of the cursors can be also done for a uvz coordinate system in which a desired angle is rotated for the original xyz coordinate system by rotating the coordinate axes by means of the rotating means for coordinate axes 8. Detailed description is as follows.

Figure 7:
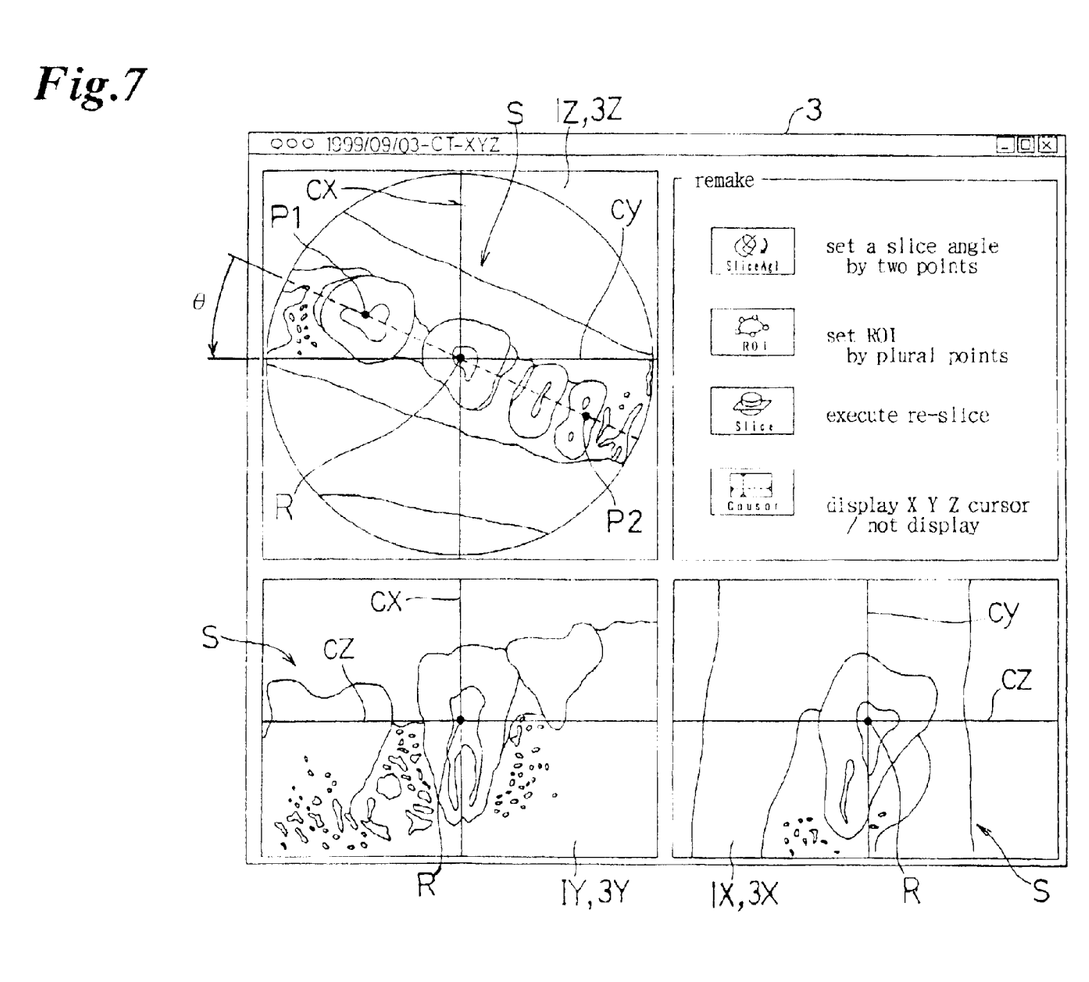
FIG. 7 shows one example of designation method of a rotation angle applied in a display method of sectional images of the present invention.
Figure 8:
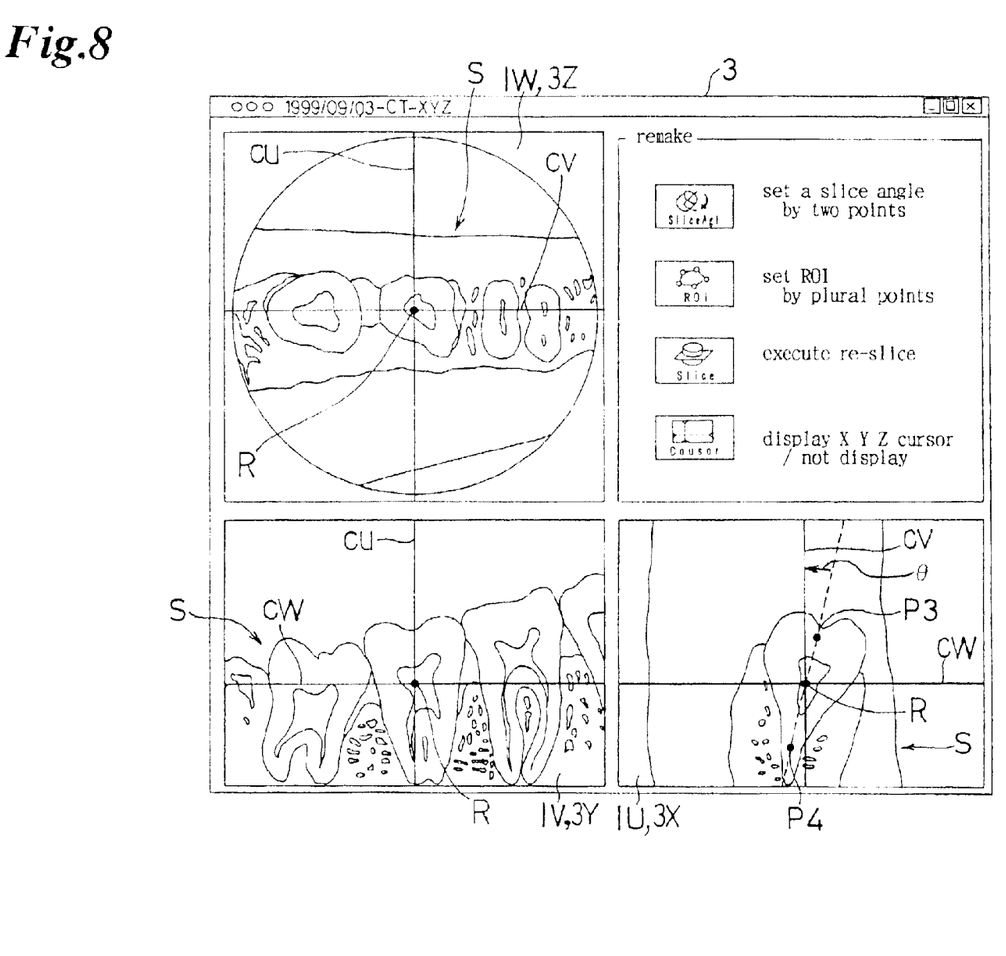
FIG. 8 shows a further designation method of a rotation angle on a remade screen by rotating as designated in FIG. 7.
Figure 9:
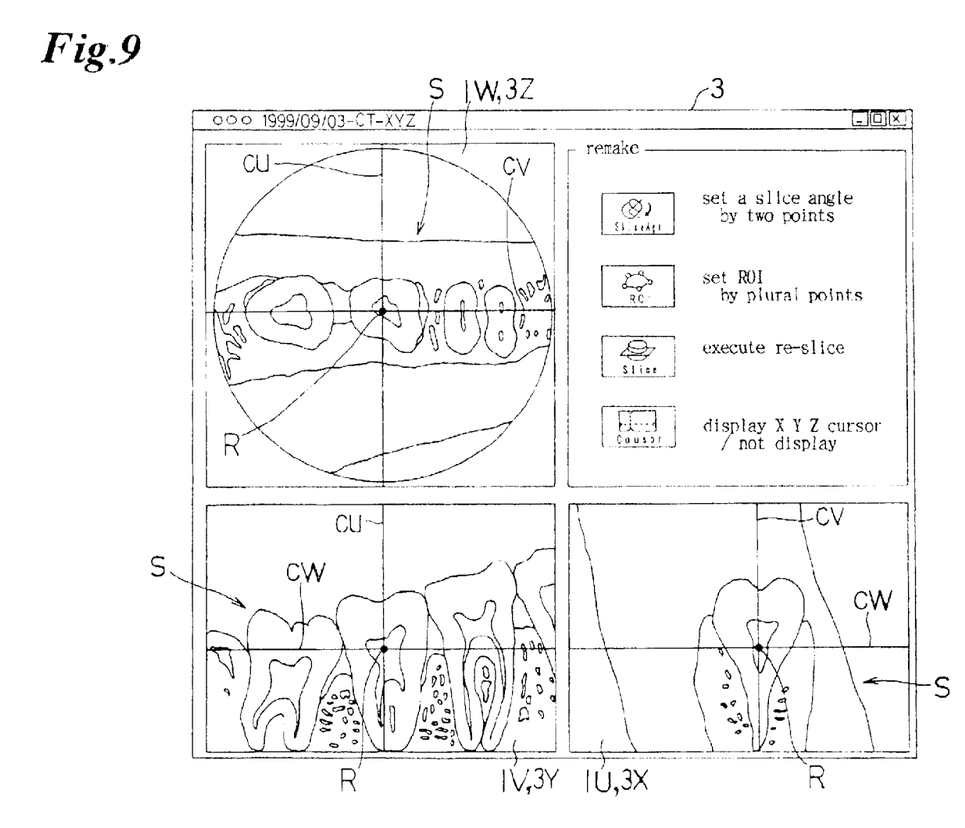
FIG. 9 shows a remade screen by rotating as mentioned in FIG. 8.

FIG. 7 shows one example of designation method of a rotation angle applied in a display method of sectional images of the present invention. FIG. 8 shows a further designation method of a rotation angle on a remade screen by rotating as designated in FIG. 7. FIG. 9 shows a remade screen by rotating as mentioned in FIG. 8.

In FIG. 7 the sectional images IX of X-section, IY of Y-section, and IZ of Z-section are displayed on the screen 3 for the same three-dimensional area S as in FIG. 1 while the area S is slant in some degree in the Z-coordinate surface of the xyz coordinate system. Then a button of "setting a slice angle by two points" is clicked so as to enter a mode for designating a rotation angle of the coordinate axes.

When two points P1 and P2 are designated on the Z-sectional image IZ, a straight line P1–P2 connecting these two points is displayed. When the straight line P1–P2 is held by pressing with the mouse 4B and for example rotated so as to be the Y-cursor cy of the Z-sectional images IZ, the rotation angle θ of the line P1–P2 for a center R of the Z-sectional images IZ is determined.

Next, when a button of "execute re-slice" is clicked, the xyz coordinate system is rotated at the angle θ around the coordinate axis perpendicular to the Z-sectional images IZ, namely z-axis, by means of the rotating means for coordinate axes 8. Thus new uvw coordinate system is produced.

There is a relation like following coordinate transformation formula between the uvw coordinate system and the xyz coordinate system.

A coordinate transformation formula for rotating at θ (rad) in counterclockwise around the z-axis:

$$\begin{bmatrix} u \\ v \\ w \\ 1 \end{bmatrix} = \begin{bmatrix} \cos(\theta) & -\sin(\theta) & 0 & 0 \\ \sin(\theta) & -\cos(\theta) & 0 & 0 \\ 0 & 0 & 1 & 0 \\ 0 & 0 & 0 & 1 \end{bmatrix} = \begin{bmatrix} x \\ y \\ z \\ 1 \end{bmatrix}$$

A coordinate transformation formula for rotating at θ (rad) in counterclockwise around the x-axis:

$$\begin{bmatrix} u \\ v \\ w \\ 1 \end{bmatrix} = \begin{bmatrix} 1 & 0 & 0 & 0 \\ 0 & \cos(\theta) & -\sin(\theta) & 0 \\ 0 & \sin(\theta) & \cos(\theta) & 0 \\ 0 & 0 & 0 & 1 \end{bmatrix} = \begin{bmatrix} x \\ y \\ z \\ 1 \end{bmatrix}$$

A coordinate transformation formula for rotating at θ (rad) in counterclockwise around the y-axis:

$$\begin{bmatrix} u \\ v \\ w \\ 1 \end{bmatrix} = \begin{bmatrix} \cos(\theta) & 0 & \sin(\theta) & 0 \\ 0 & 1 & 0 & 0 \\ -\sin(\theta) & 0 & \cos(\theta) & 0 \\ 0 & 0 & 0 & 1 \end{bmatrix} = \begin{bmatrix} x \\ y \\ z \\ 1 \end{bmatrix}$$

Then sectional images are hewn or sliced out for a new uvw coordinate system like the original xyz coordinate system and displayed on the screen 3 as shown in FIG. 8.

In FIG. 8 the reference marks cu, cv, and cw show a U-cursor, a V-cursor, and a W-cursor respectively on the new rotated uvw coordinate system and the reference marks IU, IV, and IW show a U-sectional image, a V-sectional image, and a W-sectional image on the new uvw coordinate system respectively.

As shown in FIG. 8 the three-dimensional area S is directed to be along the coordinate system on the W-sectional images IW and sectional images of three-dimensional area S which are desired to be seen from the desired direction by an operator.

It is realized from the U-sectional image IU that a planted direction of teeth and a direction of the V-cursor cv are inclined in some degree on the screen 3. When a sectional image seen from a direction orthogonal to the planted direction of teeth is desired in such a condition, further a button "setting slice angle by two points" is clicked to enter a rotation angle designation mode, two points P3 and P4 are designated, a rotation angle θ is determined by rotating the straight line P3–P4 so as to be the V-cursor cv so as to rotate a coordinate axis, sectional images are correspondingly hewn out for the new uvw coordinate system, and the sectional images are shown on the screen 3 as shown in FIG. 9.

Sectional images can be serially displayed on the screen 3 by moving cursors as shown in FIG. 1, FIG. 2, and FIG. 3.

Thus according to the display method and system of sectional images of the present invention, sectional images can be displayed in serial while moving cursors on the original coordinate system so that images desired to be observed can be quickly and easily found out. Further as stated herein, sectional images can be also displayed in serial by rotating coordinate axes to a direction desired to be seen so that sectional images of desired area which are seen from a desired direction can be quickly and easily obtained.

Figure 10:
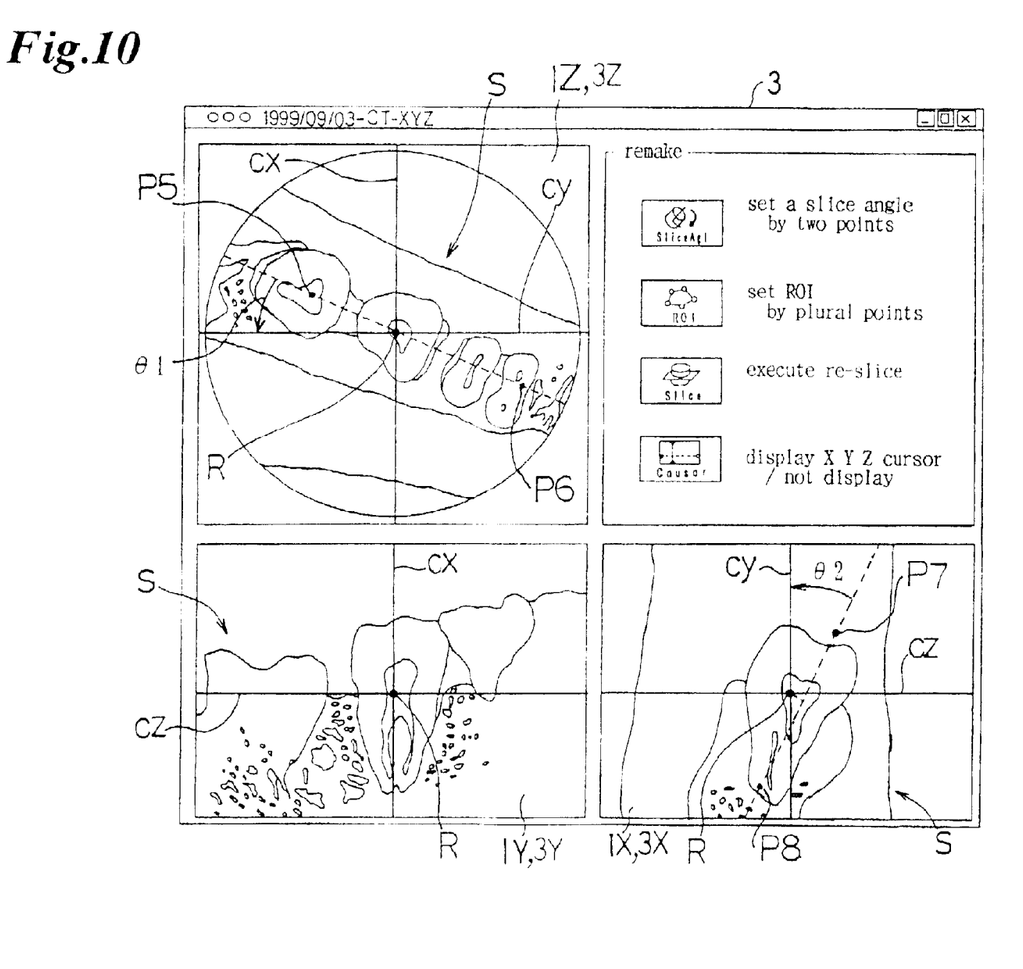
FIG. 10 shows another example of a designation method of rotation angle applied in a display method of sectional images of the present invention.

FIG. 10 shows another example of a designation method of a rotation angle applied in a display method of sectional images of the present invention.

According to the designation method, plural rotation angles around coordinate axes among three axes of x, y, and z of original xyz coordinate system are designated at the same time as shown in FIG. 7 and FIG. 8 unlike a rotation direction and rotation angle of one cursor are designated to rotate a coordinate axis each time.

Such a method is explained for the three-dimensional area S displayed by the same xyz-coordinate system as FIG. 7.

When "set slice angle by two points" is clicked on the screen 3 shown like FIG. 7, the screen 3 becomes an angle set mode.

Here points P5 and P6 are designated on the Z-dimensional image IZ, the straight line P5–P6 is similarly rotated, then a rotation angle θ1 is obtained. Next points P7 and P8 are designated on the X-dimensional image IX, the straight line P7–P8 is similarly rotated, then a rotation angle θ2 is obtained. Thereafter, a button of "execute re-slice" is clicked, at first a coordinate rotation around the z-axis at the rotation angle θ1 is executed by the coordinate axis rotation means 8. Then a coordinate rotation around the x-axis at the rotation angle θ2 is executed. Next sectional images are hewn or sliced out on a new uvw coordinate system and displayed on the screen 3. The displayed content is the same as FIG. 9.

Here list display of sectional images which is a further characteristic of the present display method of sectional images is explained.

Figure 11:
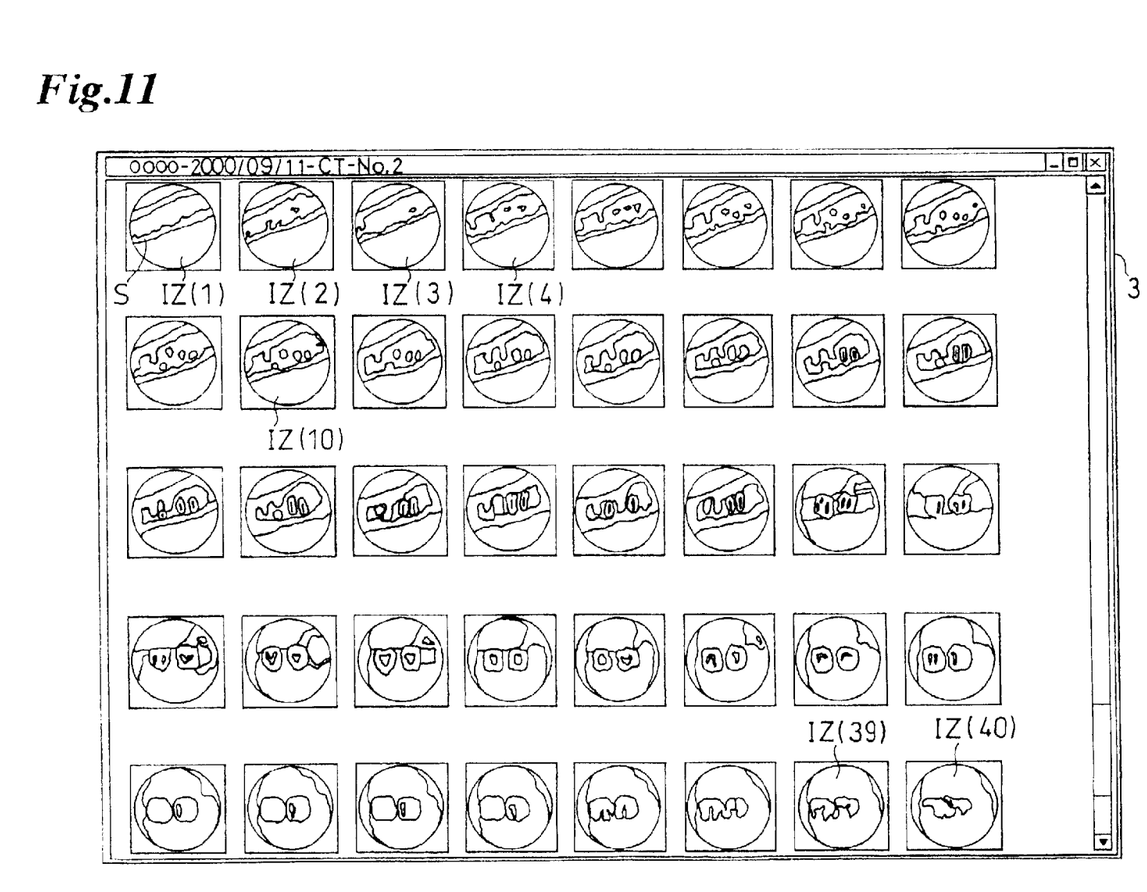
FIG. 11 shows one example of a screen displaying sectional images in list as list displaying mode according to a display method of sectional images of the present invention.
Figure 12:
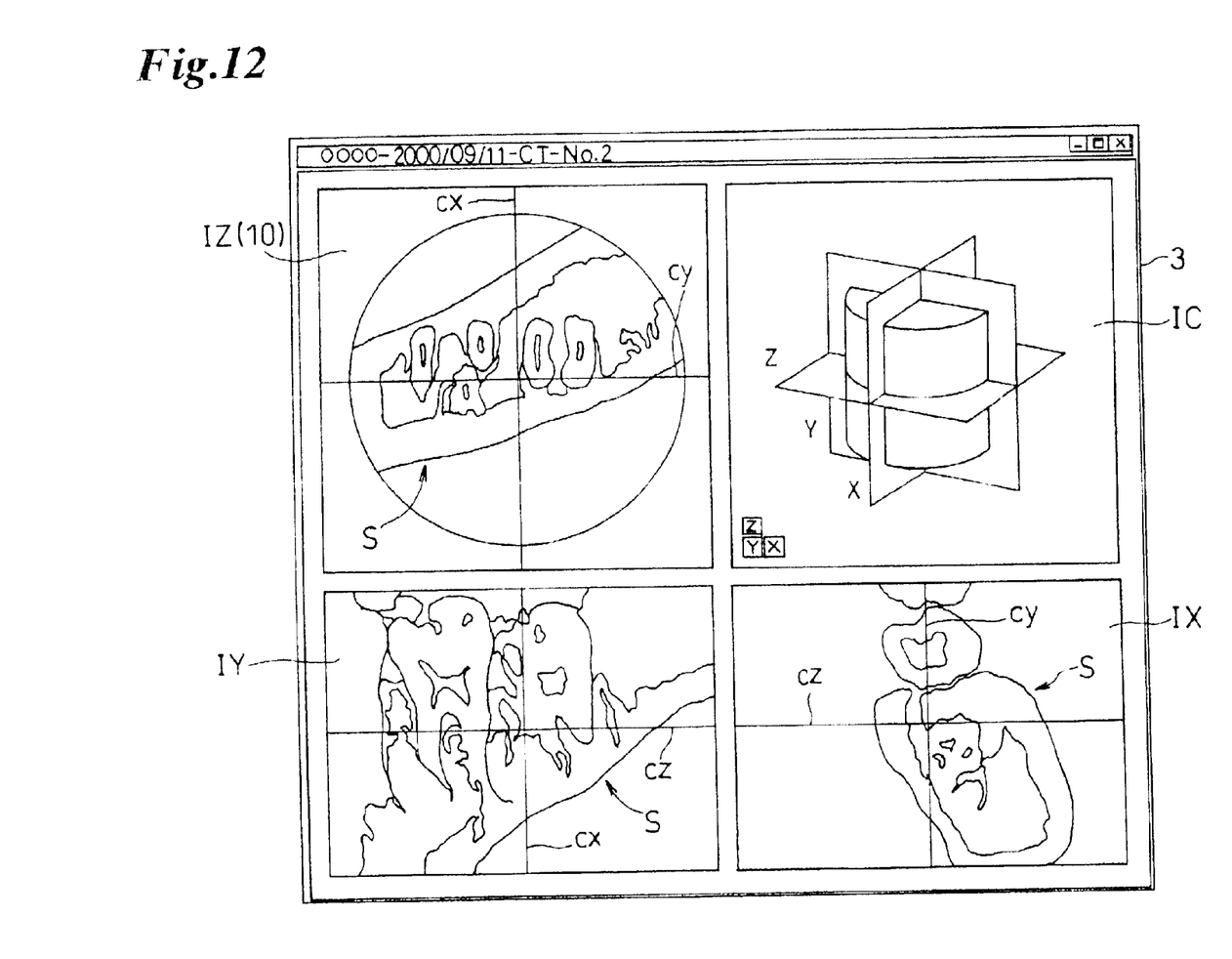
FIG. 12 shows one example of a screen displaying the three sectional images as three sectional displaying mode including sectional images selected in the screen of FIG. 11.

FIG. 11 shows one example of a screen displaying sectional images in list as a list displaying mode according to a display method of sectional images of the present invention. FIG. 12 shows one example of a screen displaying the three sectional images in array including sectional images selected in the screen of FIG. 11 as three sectional displaying mode.

After a prescribed switching operation, for example double clicking the Z-sectional image IZ or selecting the Z-sectional image IZ, on the screen of FIG. 1, a left button of a mouse is clicked to show a pull-down menu and "list display" is selected, then a list display of sectional images like FIG. 11 is shown on the screen.

In the figure Z-sectional images IZ (1)–(40) hewn out the three-dimensional area S in Z-axis direction at a fixed time interval are reduced and displayed in a list on one screen.

In this example 40 Z-sectional images IZ which are obtained by dividing the three-dimensional area S into 40 equal parts and seen in positive Z-axis direction, namely seen from above, are laid out from left to right and from top to bottom. The Z-sectional image IZ (1) is the lowest sectional image, as the number in parentheses increases, the image show upper section, and the Z-sectional image IZ (40) is the highest sectional image.

An operator can select a desired Z-sectional image IZ at a glance depending on a purpose of medical care from a list.

For example, the Z-sectional image IZ (10) is selected, a prescribed switching operation such as double clicking the Z-sectional image IZ (10) or selecting the Z-sectional image IZ (10) is executed, pull-down menu is displayed by clicking a left button of a mouse, and "list display" is selected. Then three sectional images are displayed in array like FIG. 12, the selected Z-sectional image IZ (10) is zoomed, and the Y-sectional image IY and the Z-sectional image IZ are also displayed in array as shown in the figure.

On the screen shown in FIG. 12 the sectional images IX, IY, and IZ can be displayed in serial by moving the X-cursor cx, the Y-cursor cy, and the Z-cursor cz like FIG. 1.

Thus detailed sectional images of a desired area roughly aimed in FIG. 11 can be seen so that a problem of reduced display is dissolved. Further, as the sectional images IX, IY, and IZ are displayed in array, images can be understood by intuition. Moreover, as the sectional images are displayed sequentially by moving cursors, three-dimensional images of a desired area can be easily found out.

The image IC in FIG. 12 is a guide image which three-dimensionally shows relation of an X-sectional image, a Y-sectional image, and a Z-sectional image all of which are bases of a display of three sectional image in array to the three-dimensional area S. It is more clearly comprehended how the X-sectional image IX, the Y-sectional image IY, and the Z-sectional image IZ are hewn out from the three-dimensional area S by referring such a guide image IC.

FIG. 11 may be displayed by switching the screen like FIG. 1 as mentioned above, however a roughly aimed sectional image may be selected at first in such a manner that a list like FIG. 11 is shown after the sectional images IX, IY, IZ are hewn out and the three sectional images in array like FIG. 1 may be displayed for the selected sectional image.

Further, after selecting a sectional image, only zoom of the selected sectional image or only three-section display of X-section, Y-section, and Z-section without having an X-cursor, a Y-cursor, and a Z-cursor may be displayed.

A list display isn't limited to one kind of sectional images, for example only Z-sectional image IZ. Two kinds or three kinds of sectional images such as two or three of an X-sectional image IX, a Y-sectional image IY, and a Z-sectional image IZ may be simultaneously displayed in a list if the screen allows. If plural kinds of images are displayed in a list at the same time, plural sectional images are selected and sectional images including the selected plural kinds of images may be displayed in array.

Figure 6:
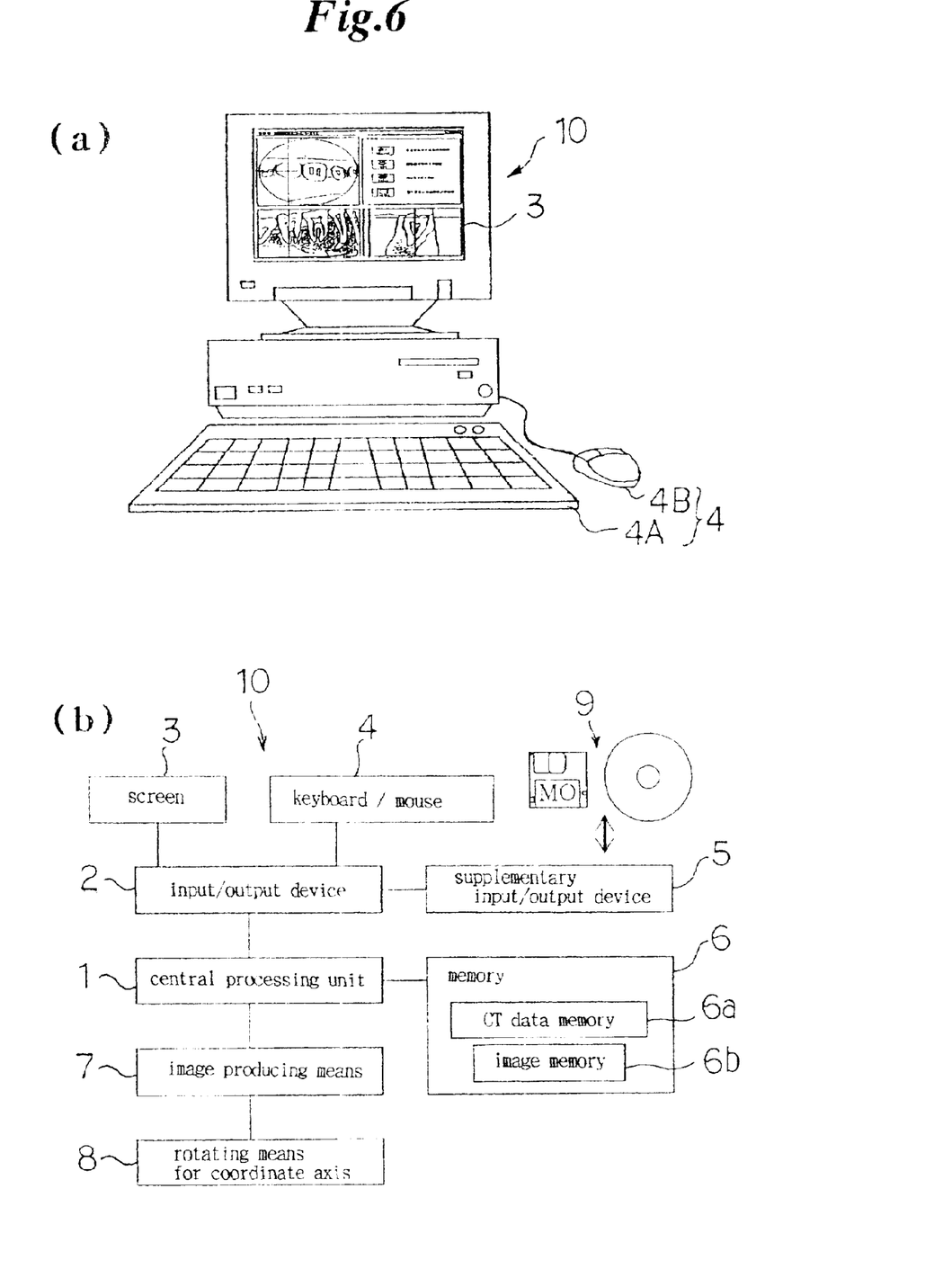
FIG. 6(a) is a external front view showing one example of a display system of sectional images of the present invention and FIG. 6(b) is a block diagram of its essential part.

A program to achieve the above-mentioned display method of sectional images can be recorded and stored in a recording medium 9 (see FIG. 6). Such a recording medium 9 is read in a normal computer to be processed so that the display method of sectional images of the present invention can be achieved.

In this embodiment, a dental arch used for dental care is shown as an example of a three-dimensional area, however this invention isn't limited to such an example and can be applied for displaying sectional images of an object in which physical data is given for each point of a three-dimensional area.

What is claimed is:

1. A display method far displaying three-dimensional data as a combination of three sectional images of an X-section, a Y-section, and a Z-section orthogonalizing each other, by processing a three-dimensional data obtained by such as CT imaging, said method comprising the steps of:

preparing in advance sectional images of sections parallel to said X-section, Y-section, and Z-section, said sectional images being sliced off data from said three-dimensional data at a predetermined interval, displaying on three display parts as a three sectional displaying mode a X-sectional image, a Y-sectional image, and a Z-sectional image, each selected from said prepared sectional images, together with an X-cursor, a Y-cursor, and a Z-cursor, each of which specifies a section of said corresponding sectional images, and when, on any one of said three display parts, at least one of said cursors displayed together with said sectional images is moved, sequentially changing a sectional image to be displayed corresponding to the moved cursor on another display part different from the display part where the cursor was moved, following the moving of the cursor, in a manner that said sectional image to be displayed on said other display part is selected from said sectional images.

2. The display method as set forth in claim 1, wherein, a uvw coordinate system defined by U-section, V-section and W-section is newly defined as a rotated coordination system relative to a xyz coordination system defined by said X-section, said Y-section and said Z-section, and wherein said method comprising the steps of:

preparing in advance sectional images of sections parallel to said U-section, V-section, and W-section, said sectional images being sliced off data from said three-dimensional data at a predetermined interval, displaying on three display parts as a three sectional displaying mode a U-sectional image, a V-sectional image, and a W-sectional image, each selected from said prepared sectional images, together with an U-cursor, a V-cursor, and a W-cursor, each of which specifies a section of said corresponding sectional images, and when, on any one of said three display parts, at least one of said cursors displayed together with said sectional images is moved, sequentially changing a sectional image to be displayed corresponding to the moved cursor on another display part different from the display part where the cursor was moved, following the moving of the cursor, in a manner that said sectional image to be displayed on said other display part is selected from said sectional images.

3. The display method as set forth in claim 2, wherein presetting of a rotational angle for said uvw coordinate system is executed by doing a specified operation on any one of display parts displaying the X-, Y-, and Z-sectional images.

4. The display method as set forth in any one of claims 1–3, wherein said three sectional images are displayed as combination of three sectional images, like as a form of three-section picture display of a three-dimensional body.

5. The display method as set forth in any one of claims 1–3, wherein said cursors are displayed on said three display parts as a combination of two cursors crossing each other, and wherein, when a crossing point of said two cursors is transversely moved on any one of said display parts, sequentially changing sectional images to be displayed corresponding to said moved cursors by moving of the crossing point on other display parts different from the display part where the cursor was moved, following the moving of the cursors, in a manner that said sectional image to be displayed on said other display part is selected from said sectional images.

6. The display method as set forth in any one of claims 1–3, wherein image display conditions of said three images are adjustable at a same level, especially in their contrast and brightness.

7. The display method as set forth in any one of claims 1–3, wherein, by a specific operation, said three sectional displaying mode is changed into a list displaying mode displaying a series of sectional images selected from said X-sectional images, Y-sectional images and Z-sectional images previously prepared, and in this state of said list displaying mode, when any sectional image is selected, by a specific operation, said list displaying mode is changed into said three sectional displaying mode displaying three sectional images including the selected sectional image.

8. The display method as set forth in any one of claims 1–3, wherein the corresponding cursor displayed on the other display part different from the display part where said moved cursor is displayed, is also correspondingly moved following the movement of said moved cursor.

9. A display apparatus for displaying three-dimensional data as a combination of three sectional images of an X-section, a Y-section, and a Z-section orthogonalizing each other, by processing a three-dimensional data obtained by such as CT imaging, comprising:

an image memory for saving prepared sectional images of sections parallel to said X-section, Y-section, and Z-section, said sectional images being sliced off data from said three-dimensional data at a predetermined interval, and a display controlling means with three-display parts for displaying a combination of an X-sectional image, a Y-sectional image, and a Z-sectional image as a three sectional displaying mode, each sectional image being selected from said sectional images previous prepared, together with an X-cursor, a Y-cursor, and a Z-cursor, each of which specifies a section of said corresponding sectional images, whereby when, on any one of said three display parts, at least one of said cursors displayed together with said sectional images is moved, a sectional image to be displayed corresponding to the moved cursor on another display part different from the display part where the cursor was moved is sequentially changed, following the moving of the cursor, in a manner that said sectional image to be displayed on said other display part is selected from said sectional images.

10. The display apparatus as set forth in claim 9, further comprising a rotating means for coordinate axis;

wherein, a uvw coordination system defined by U-section, V-section and W-section is newly defined as a rotated coordination system by said rotating means relative to a xyz coordination system defined by said X-section, said Y-section and said Z-section, wherein said image memory saves in advance prepared sectional images of sections parallel to said U-section, V-section, and W-section, said sectional images being sliced off data from said three-dimensional data at a predetermined interval, wherein by said display controlling means on said three display parts a combination of an U-sectional image, a V-sectional image, and a W-sectional image are displayed as a three sectional displaying mode, each sectional image being selected from said sectional images previous prepared, together with an U-cursor, a V-cursor, and a W-cursor, each of which specifies a section of said corresponding sectional images, and whereby when, on any one of said three display parts, at least one of said cursors displayed together with said sectional images is moved, a sectional image to be displayed corresponding to the moved cursor on another display part different from the display part where the cursor was moved is sequentially changed, following the moving of the cursor, in a manner that said sectional image to be displayed on said other display part is selected from said sectional images.

11. The display apparatus as set forth in claim 10, wherein presetting of a rotational angle for said uvw coordinate system is executed by doing a specified operation on any one of display parts displaying the X-, Y-, and Z-sectional images.

12. The display apparatus as set forth in any one of claims 9–11, wherein said three sectional images are displayed as combination of three-section images, like as a form of three-section picture display of a three-dimensional body.

13. The display apparatus as set forth in any one of claims 9–11, wherein said cursors are displayed on said three display parts as a combination of two cursors crossing each other, and wherein, when a crossing point of said two cursors is transversely moved on any one of said display parts, sequentially changing sectional images to be displayed corresponding to said moved cursors by moving of the crossing point on other display parts different from the display part where the cursor was moved, following the moving of the cursors, in a manner that said sectional image to be displayed on said other display part is selected from said sectional images.

14. The display apparatus as set forth in any one of claims 9–11, wherein image display conditions of said three images are adjustable at a same level, especially in their contrast and brightness.

15. The display apparatus as set forth in any one of claims 9–11, wherein, by a specific operation, said three sectional displaying mode is changed into a list displaying mode displaying a series of sectional images selected from said X-sectional images, Y-sectional images and Z-sectional images previously prepared, and in this state of said list displaying mode, when any sectional image is selected, by a specific operation, said list displaying mode is changed into said three sectional displaying mode displaying three sectional images including the selected sectional image.

16. The display apparatus as set forth in any one of claims 9–11, wherein the corresponding cursor displayed on the other display part different from the display part where said moved cursor is displayed, is also correspondingly moved following the movement of said moved cursor.

17. A recording medium in which a computer readable program is saved for executing the method for displaying three-dimensional data as a combination of three sectional images of an X-section, a Y-section, and a Z-section orthogonalizing each other, by processing a three-dimensional data obtained by such as CT imaging, said method comprising the steps of:

preparing in advance sectional images of sections parallel to said X-section, Y-section, and Z-section, said sectional images being sliced off data from said three-dimensional data at a predetermined interval, displaying on three display parts as a three sectional displaying mode a X-sectional image, a Y-sectional image, and a Z-sectional image, each selected from said prepared sectional images, together with an X-cursor, a Y-cursor, and a Z-cursor, each of which specifies a section of said corresponding sectional images, and when, on any one of said three display parts, at least one of said cursors displayed together with said sectional images is moved, sequentially changing a sectional image to be displayed corresponding to the moved cursor on another display part different from the display part where the cursor was moved, following the moving of the cursor, in a manner that said sectional image be displayed on said other display part is selected from said sectional images.

18. The recording medium as set forth in claim 17, wherein, a uvw coordination system defined by U-section, V-section and W-section is newly defined as a rotated coordination system relative to a xyz coordination system defined by said X-section, said Y-section and said Z-section, and wherein said method comprising the steps of:

preparing in advance sectional images of sections parallel to said U-section, V-section, and W-section, said sectional images being sliced off data from said three-dimensional data at a predetermined interval, displaying on three display parts as a three sectional displaying mode a U-sectional image, a V-sectional image, and a W-sectional image, each selected from said prepared sectional images, together with an U-cursor, a V-cursor, and a W-cursor, each of which specifies a section of said corresponding sectional images, and when, on any one of said three display parts, at least one of said cursors displayed together with said sectional images is moved, sequentially changing a sectional image to be displayed corresponding to the moved cursor on another display part different from the display part where the cursor was moved, following the moving of the cursor, in a manner that said sectional image to be displayed on said other display part is selected from said sectional images.

19. The recording medium as set forth in claim 18, wherein presetting of a rotational angle for said uvw coordinate system is executed by doing a specified operation on any one of display parts displaying the X-, Y-, and Z-sectional images.

20. The recording medium as set forth in any one of claims 17–19, wherein said three sectional images are displayed as combination of three-section images, like as a form of three-section picture display of a three-dimensional body.

21. The recording medium as set forth in any one of claims 17–19, wherein said cursors are displayed on said three display parts as a combination of two cursors crossing each other, and wherein, when a crossing point of said two cursors is transversely moved on any one of said display parts, sequentially changing sectional images to be displayed corresponding to said moved cursors by moving of the crossing point on other display parts different from the display part where the cursor was moved, following the moving of the cursors, in a manner that said sectional image to be displayed on said other display part is selected from said sectional images.

22. The recording medium as set forth in any one of claims 17–19, wherein image display conditions of said three images are adjustable at a same level, especially in their contrast and brightness.

23. The recording medium as set forth in any one of claims 17–19, wherein, by a specific operation, said three sectional displaying mode is changed into a list displaying mode displaying a series of sectional images selected from said X-sectional images, Y-sectional images and Z-sectional images previously prepared, and in this state of said list displaying mode, when any sectional image is selected, by a specific operation, said list displaying mode is changed into said three sectional displaying mode displaying three sectional images including the selected sectional image.

24. The recording medium as set forth in any one of claims 17–19, wherein the corresponding cursor displayed on the other display part different from the display part where said moved cursor is displayed, is also correspondingly moved following the movement of said moved cursor.

* * * * *